US009770508B2

(12) United States Patent
Günther et al.

(10) Patent No.: US 9,770,508 B2
(45) Date of Patent: Sep. 26, 2017

(54) SEMIFLUORINATED ALKANE COMPOSITIONS

(71) Applicant: Novaliq GmbH, Heidelberg (DE)

(72) Inventors: Bernhard Günther, Dossenheim (DE); Dieter Scherer, Laufen (CH); Anthony Pettigrew, Heidelberg (DE)

(73) Assignee: NOVALIQ GMBH, Heidelberg (DE)

(*) Notice: Subject to any disclaimer, the term of this patent is extended or adjusted under 35 U.S.C. 154(b) by 0 days.

(21) Appl. No.: 14/427,969

(22) PCT Filed: Sep. 12, 2013

(86) PCT No.: PCT/EP2013/068909
§ 371 (c)(1),
(2) Date: Mar. 12, 2015

(87) PCT Pub. No.: WO2014/041071
PCT Pub. Date: Mar. 20, 2014

(65) Prior Publication Data
US 2015/0238605 A1    Aug. 27, 2015

(30) Foreign Application Priority Data

Sep. 12, 2012  (EP) .................................... 12183997
May 27, 2013   (EP) .................................... 13169399

(51) Int. Cl.
*A61K 31/232*    (2006.01)
*A61K 31/202*    (2006.01)
*A61K 47/06*     (2006.01)
*A61K 45/06*     (2006.01)
*A61K 9/00*      (2006.01)
*A61K 9/08*      (2006.01)
*A61K 31/436*    (2006.01)
*A61K 31/07*     (2006.01)
*A61K 31/11*     (2006.01)
*A61K 31/203*    (2006.01)
*A61K 31/4418*   (2006.01)
*A61K 31/02*     (2006.01)

(52) U.S. Cl.
CPC ............ *A61K 47/06* (2013.01); *A61K 9/0048* (2013.01); *A61K 9/08* (2013.01); *A61K 31/02* (2013.01); *A61K 31/07* (2013.01); *A61K 31/11* (2013.01); *A61K 31/202* (2013.01); *A61K 31/203* (2013.01); *A61K 31/232* (2013.01); *A61K 31/436* (2013.01); *A61K 31/4418* (2013.01); *A61K 45/06* (2013.01)

(58) Field of Classification Search
CPC .... A61K 9/0048; A61K 47/06; A61K 31/232; A61K 31/202; A61K 9/08
See application file for complete search history.

(56) References Cited

U.S. PATENT DOCUMENTS

| | | |
|---|---|---|
| 2,616,927 A | 11/1952 | Kauck et al. |
| 5,077,036 A | 12/1991 | Long |
| 5,326,566 A | 7/1994 | Parab |
| 5,336,175 A | 8/1994 | Mames |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers |
| 5,981,607 A | 11/1999 | Ding et al. |
| 6,042,845 A | 3/2000 | Sun et al. |
| 6,113,919 A | 9/2000 | Reiss et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,372,243 B2 | 4/2002 | Kobuch |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz et al. |
| 7,001,607 B1 | 2/2006 | Menz et al. |
| 7,026,359 B1 | 4/2006 | Gross |
| 7,258,869 B1 | 8/2007 | Berry et al. |
| 7,740,875 B2 | 6/2010 | Dechow |
| 8,029,977 B2 | 10/2011 | Meinert et al. |
| 8,470,873 B2 | 6/2013 | Chen |
| 8,614,178 B2 | 12/2013 | Theisinger et al. |
| 8,986,738 B2 | 3/2015 | Meinert |
| 9,241,900 B2 | 1/2016 | Wilson |
| 9,308,262 B2 | 4/2016 | Günther et al. |

(Continued)

FOREIGN PATENT DOCUMENTS

| | | |
|---|---|---|
| EP | 0 089 815 | 9/1983 |
| EP | 0 670 159 A1 | 9/1995 |

(Continued)

OTHER PUBLICATIONS

Dias et al., Fluid Phase Equilibria 222-23, 325-30 (2004).*
Costa Gomes et al., J. Fluorine Chem. 125, 1325-29 (2004).*
Gerdenitsch, "Emulsions—established and promising drug carriers for parenteral adminstration", retrieved from internet: http://ipimediaworld.com/wp-content/uploads/2012/05/Pages-from-IPI-Volume-2-Issue-1-11.pdf. Date Accessed: Jul. 20, 2016.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.

(Continued)

*Primary Examiner* — Theodore R West
(74) *Attorney, Agent, or Firm* — Hoxie & Associates LLC

(57) ABSTRACT

The invention provides novel compositions comprising semifluorinated alkanes and at least one compound sensitive or prone to oxidation. The compositions can be used as medicines that are topically administered to an eye or ophthalmic tissue. The invention further provides kits comprising such compositions.

20 Claims, No Drawings

(56) References Cited

U.S. PATENT DOCUMENTS

| | | |
|---|---|---|
| 2002/0128527 A1 | 9/2002 | Meinert |
| 2003/0018044 A1 | 1/2003 | Peyman |
| 2003/0027833 A1 | 2/2003 | Cleary et al. |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson et al. |
| 2005/0079210 A1 | 4/2005 | Gupta |
| 2005/0175541 A1 | 8/2005 | Lanza et al. |
| 2008/0207537 A1 | 8/2008 | Turner et al. |
| 2008/0260656 A1 | 10/2008 | Mallard |
| 2009/0149546 A1 | 6/2009 | Chang |
| 2010/0008996 A1 | 1/2010 | Meinert |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Gunther et al. |
| 2014/0140942 A1 | 5/2014 | Gunther et al. |
| 2014/0369993 A1 | 12/2014 | Gunther et al. |
| 2015/0224064 A1 | 8/2015 | Günther et al. |
| 2016/0101178 A1 | 4/2016 | Wilson |
| 2016/0159902 A1 | 6/2016 | Günther et al. |

FOREIGN PATENT DOCUMENTS

| | | |
|---|---|---|
| EP | 0 965 329 A1 | 12/1999 |
| EP | 0 965 334 A1 | 12/1999 |
| EP | 0 939 655 B1 | 6/2002 |
| EP | 1 152 749 B1 | 4/2006 |
| EP | 2 110 126 A1 | 10/2009 |
| EP | 2 332 525 A1 | 6/2011 |
| EP | 2 335 735 A1 | 6/2011 |
| EP | 2 462 921 A1 | 6/2012 |
| JP | S6452722 | 2/1989 |
| JP | 2000511157 | 8/2000 |
| WO | WO 96/40052 A1 | 12/1996 |
| WO | WO 97/12852 A1 | 4/1997 |
| WO | WO 00/24376 A1 | 5/2000 |
| WO | WO 00/54588 A1 | 9/2000 |
| WO | WO 02/49631 A1 | 6/2002 |
| WO | WO 2005/099718 A1 | 10/2005 |
| WO | WO 2005/099752 | 10/2005 |
| WO | WO 2005/123035 A1 | 12/2005 |
| WO | WO 2006/007510 A1 | 1/2006 |
| WO | WO 2006/042059 | 4/2006 |
| WO | WO 2006/048242 | 5/2006 |
| WO | WO 2007/052288 A2 | 5/2007 |
| WO | WO 2008/060359 A2 | 5/2008 |
| WO | WO 2009/013435 | 1/2009 |
| WO | WO 2010/062394 A2 | 6/2010 |
| WO | WO 2010/146536 | 12/2010 |
| WO | WO 2011/009436 | 1/2011 |
| WO | WO 2011/073134 A1 | 6/2011 |
| WO | WO 2012/052418 A1 | 4/2012 |
| WO | WO 2012/062834 A1 | 5/2012 |
| WO | WO 2012/093113 A1 | 7/2012 |
| WO | WO 2012/121754 | 9/2012 |
| WO | WO 2012/160179 A2 | 11/2012 |
| WO | WO 2012/160180 A2 | 11/2012 |
| WO | WO 2013/110621 A1 | 8/2013 |
| WO | WO 2014/041055 A1 | 3/2014 |
| WO | WO 2015/011199 | 1/2015 |

OTHER PUBLICATIONS

U.S. Appl. No. 14/427,927, filed Mar. 12, 2015, Gunther et al.
Ahmed, I. et al., "Disposition of Timolol and Inulin in the Rabbit Eye Following Corneal Versus Non-Corneal Absorption," International Journal of Pharmaceutics, 1987, 38, 9-21.
Baerdemaeker, L. et al., "Pharmacokinetics in Obese Patients," Continuing Education in Anaesthesia, Critical Care & Pain, 2004, 4, 152-155.
Broniatowski, M. et al., "Langmuir Monolayers Characteristic of (Perfluorodecyl)-Alkanes," Journal of Physical Chemistry B, 2004, 108, 13403-13411.
Chemical Book, 5-Fluorouracil, available at <http://www.chemicalbook.com/ChemicalProductProperty_EN_CB8162744.htm>, accessed Mar. 7, 2014, 1 page.
Davies, N., "Biopharmaceutical Considerations in Topical Ocular Drug Delivery," Clinical and Experimental Pharmacology and Physiology, 2000, 27, 558-562.
Dembinski, R. et al., "Semi-fluorinated Alkanes as Carriers for Drug Targeting in Acute Respiratory Failure," Experimental Lung Research, 2010, 36, 499-507.
Elkeeb, R. et al., "Transungual Drug Delivery: Current Status," International Journal of Pharmaceutics, 2010, 384, 1-8.
English-language machine translation of EP0670159 (A1) issued in U.S. Appl. No. 14/122,025 on Apr. 1, 2015, 10 pages.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Gayton, J., "Etiology, Prevalence, and Treatment of Dry Eye Disease," Clinical Ophthalmology, 2009, 3, 405-412.
Griffin, W., "Classification of Surface-Active Agents by 'HLB'," Journal of the Society of Cosmetic Chemists, 1949, 1, 311-326.
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Preliminary Report on Patentability for International Application No. PCT/EP2013/068882 dated Mar. 17, 2015, 5 pages.
International Preliminary Report on Patentability for International Application No. PCT/EP2013/068909 dated Mar. 17, 2015, 7 pages.
International Search Report for International Application No. PCT/EP2011/068141 mailed Dec. 14, 2011, 2 pages.
International Search Report for International Application No. PCT/EP2011/069795 mailed Jan. 16, 2012, 3 pages.
International Search Report for International Application No. PCT/EP2012/050043 mailed Apr. 24, 2012, 2 pages.
International Search Report for International Application No. PCT/EP2012/059787 mailed Dec. 5, 2012, 4 pages.
International Search Report for International Application No. PCT/EP2012/059788 mailed Dec. 3, 2012, 4 pages.
International Search Report for International Application No. PCT/EP2013/051163 mailed Mar. 4, 2013, 4 pages.
International Search Report for International Application No. PCT/EP2013/068882 mailed Oct. 30, 2013, 4 pages.
International Search Report for International Application No. PCT/EP2013/068909 mailed Dec. 5, 2013, 4 pages.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.

(56) References Cited

OTHER PUBLICATIONS

Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.

Lemp, M., "Management of Dry Eye Disease," The American Journal of Managed Care, 2008, 14 (3), S88-S101.

Mackiewicz, J. et al., "In Vivo Retinal Tolerance of Various Heavy Silicone Oils," Investigative Ophthalmology & Visual Science, 2007, 48 (4), 1873-1883.

Meinert, H. et al., "The Use of Semifluorinated Alkanes in Blood-Substitutes," Biomaterials, Artificial Cells, and Immobilization Biotechnology, 1993, 21 (5), 583-595.

Meinert, H. et al., "Semifluorinated Alkanes—A New Class of Compounds with Outstanding Properties for Use in Ophthalmology," European Journal of Ophthalmology, 2000, 10 (3), 189-197.

Murdan, S., "Enhancing the Nail Permeability of Topically Applied Drugs," Expert Opinion on Drug Delivery, 2008, 5 (11), 1267-1282.

Perry, H., "Dry Eye Disease: Pathophysiology, Classification, and Diagnosis," The American Journal of Managed Care, 2008, 14 (3), S79-S87.

Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, abstract only.

Plassmann, M. et al., "Trace Analytical Methods for Semifluorinated n-Alkanes in Snow, Soil, and Air," Analytical Chemistry, 2010, 82 (11), 4551-4557.

Plassmann, M. et al., "Theoretical and Experimental Simulation of the Fate of Semifluorinated n-Alkanes During Snowmelt," Environmental Science & Technology, 2010, 44 (17), 6692-6697.

Rosca-Casian, O. et al., "Antifungal Activity of *Aloe vera* Leaves," Fitoterapia, 2007, 28, 219-222.

Rosenberg, A., "Effects of Protein Aggregates: An Immunologic Perspective," The AAPS Journal, 2006, 8 (3), E501-E507.

Stevenson, C., "Characterization of Protein and Peptide Stability and Solubility in Non-Aqueous Solvents," Current Pharmaceutical Biotechnology, 2000, 1, 165-182.

Wang, W., "Lyophilization and Development of Solid Protein Pharmaceuticals," International Journal of Pharmaceutics, 2000, 203, 1-60.

Wong, D. et al., "Perfluorocarbons and Semifluorinated Alkanes," Seminars in Ophthalmology, 2000, 15 (1), 25-35.

Blackie et al., "MGD: Getting to the Root Cause of Dry Eye", Review of Optometry, 2012, pp. 1-12.

Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.

Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No: PSa03-02, English Translation, 6 pages.

Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.

Troiano et al., "Effect of Hyptonic .4% Hyaluronic Acid Drops in Dry Eye Patients: A Cross-Study", Cornea 27(10): 1126-1130 (Abstract Only).

Sato et al., "Vitrectomy and Intraocular Lens Implantation for Cytomegalovirus Retinitis in a Patient with Acquired Immunodeficiency Syndrome", Presented by Medical Online, New Ophthalmology, 1999, 16(7):995-998 (4 pages).

Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.

Spöler et al., "Towards a New in vitro Model of Dry Eye: The ex vivo Eye Irritation Test," Developments in Ophthalmology, 2010, 45: 93-107.

\* cited by examiner

SEMIFLUORINATED ALKANE COMPOSITIONS

CROSS REFERENCE TO RELATED APPLICATIONS

This application is the National Stage Entry under 35 U.S.C. §371 of International Application No. PCT/EP2013/068909 filed Sep. 12, 2013, which claims priority to European Patent Application No. 12183997.1 filed Sep. 12, 2012, and European Patent Application No. 13169399.6 filed May 27, 2013, the contents of each of which are incorporated herein by reference.

FIELD

The present invention is in the field of compositions comprising oxidation-prone pharmaceutically active ingredients, specifically compositions that are based on semifluorinated alkanes. In particular, the compositions of the present invention may be topical ophthalmic compositions useful in the treatment of ocular diseases or conditions.

BACKGROUND

The stability of an active pharmaceutical compound during storage over a variety of conditions is a generally of concern during development of a formulation for the compound. This aspect is especially relevant for liquid formulations of compounds which are sensitive and/or prone to decomposition via oxidation pathways. It is becoming even more relevant today as countries with hot and moderately humid climate (i.e. ICH zone IVb countries) are becoming increasingly important to pharmaceutical companies so that new drug formulations are needed which take into account the higher temperatures and humidifies of these countries.

Oxidation may be promoted thermally, photolytically, or by chemical means. Compounds comprising aliphatic double bond systems are, in particular, sensitive towards degradation by oxidation, often via free-radical chain processes with molecular oxygen.

Such processes, known also as auto-oxidation, generally begins via an initiation process in which a free-radical is generated (e.g. via abstraction of a hydrogen atom by an initiator radical), followed by propagation steps involving oxygen and further compound molecules. Termination may occur when two radical products couple. Compounds comprising free-radical stabilizing aliphatic double bond configurations such as the methylene-interrupted polyene systems of polyunsaturated lipid derivatives are generally more susceptible to auto-oxidation. These and other oxidation processes can readily lead to, over time, the formation and accumulation of undesirable and pharmaceutically ineffective reaction products. Some of the degradants may be harmful or toxic.

The use of antioxidants and/or stabilizer excipients remains one of the foremost strategies for mitigating or preventing the oxidation of such compounds and to increase shelf-life. Typical antioxidants are butylated hydroxytoluene (BHT), ascorbic acid, tocopherol derivatives etc. Many antioxidants will act as free-radical scavengers; and act by terminating free-radicals and inhibiting the chain processes. Excipients which can act as metal ion chelators e.g. ethylene diamine tetraacetic acid (EDTA) may also be used to limit the effect of trace heavy metal impurities which can also catalyse oxidation reactions. The encapsulation or shielding of oxidation-sensitive compounds, such as with liposomes or cyclodextrins are also known methods of preventing degradation.

A further measure to prevent oxidative degradation of such compounds would be the removal of oxygen dissolved in the liquid vehicle through sparging with an inert gas, with for example, nitrogen. This is however process-intensive and not cost-effective, and requires, in addition, special attention during further processing steps and with packaging to prevent the reintroduction of atmosphere.

Polyunsaturated fatty acids (often abbreviated as PUFA) are a class of compounds that are prone to oxidative degradation. These include omega fatty acids such as omega-3 fatty acids (also known as ω-3 fatty acids or n-3 fatty acids) and omega-6 fatty acids (also known as ω-6 fatty acids or n-6 fatty acids). These are essential fatty acids because they are available only through dietary intake, and because they involved in many human metabolic processes and functions. As such, they have been implicated as beneficial in the treatment or prophylaxis of a wide variety of different health conditions.

For example, these compounds have been found to be useful for the topical treatment and prevention of ocular pathologies such as dry eye disease (DED). DED, also known as keratoconjunctivitis sicca or dysfunctional tear syndrome, is a multifunctional disorder of the tear film and ocular surface which results in discomfort, visual disturbance, and often even in ocular surface damage. The loss in dynamic stability of the structure, composition, volume and distribution, as well as clearance of the tear film can lead to the development of DED.

An inflammation cycle is one of the key processes that maintain and potentially progress the dry eye condition. Omega fatty acids, in relation to their anti-inflammatory properties, have been found to reduce the severity of DED and its symptoms and improve tear secretion. Omega-3 fatty acids, in particular, have been associated with the modulation of the production of anti-inflammatory and immunomodulatory eicosanoid prostaglandins such as PGE1. They are also implicated in suppressing the expression of pro-inflammatory cytokines such as IL-1 and TNF-α, which are associated with dry eye disease.

The formulation of such active ingredients prone to oxidation into topical ophthalmic compositions such as eye drops can however be challenging. The choices of excipients, and therefore antioxidants and stabilizers which can be used are more limited due to incompatibility, toxicity or poor tolerance with the ocular surface. At the same time, however, the minimization of degradation (resulting in colour changes of the preparation, precipitation of insoluble materials, etc.) becomes more acute.

Compositions comprising omega fatty acids for the topical treatment of the dry eye condition and its symptoms are however known in the art. Gastrointestinal intolerance resulting from the oral ingestion of large quantities of these fatty acids as supplements (and systemic absorption effect) can be avoided with direct and local administration of these active molecules to the surface of the eye.

For example, Remogen® Omega (marketed by TRB Chemedica International S.A.), is a commercially available ophthalmic preparation comprising omega fatty acids that indicated for dry eye conditions. As disclosed in its product information, the preparation is a hypotonic hydrogel containing eicosapentaenoic acid (EPA) and docosahexaenoic acid (DHA), antioxidant vitamin E (tocopheryl acetate), the emollient substances carbopol 980, glycerol, pemulen, and sodium hydroxide, disodium phosphate, and distilled water.

The hydrogel composition itself is described as a microemulsion, with a dispersion of the lipidic molecules (fatty acids and vitamin E). The product is packaged in the form of single-dose containers packed in an aluminium pouch, with the recommendation to discard the product immediately after use. With respect to stability, storage is suggested to be in a refrigerator at 2-8° C., with a shelf-life of 3 months if stored, at below 25° C., unrefrigerated. Due to its poor thermal stability, the product is shipped in a cold chain, i.e. transported in refrigerated containers and stored at the warehouse and in the pharmacy under refrigeration. Thus the consignment is expensive and requires a substantial effort in terms of temperature monitoring and logistics.

Similar, if not the same type of ophthalmic hydrogel compositions are also disclosed in US 2012/0010280. It is described that the fatty acids are in solution in the antioxidant tocopheryl acetate, with the tocopheryl acetate present in amounts of up to 75% by weight of the oily mixture. These are dispersed as oily droplets in the hydrogel. Aqueous emulsions comprising a combination of omega-3 and omega-6 fatty acids, and surfactant (e.g. Tween 80), Glucam E-20, and a drop of vitamin E as an antioxidant were found to be poorly adapted for maintaining stability of the omega fatty acids are proposed in WO 2006/007510. It should be noted, however, that emulsion systems based on hydrogels, with their generally increased viscosity and bioadhesive properties may incur, upon instillation and also during its contact time to the ocular surface, irritating foreign body sensation and blurred vision. Depending also on the degree of their viscosity, these may be more difficult to dispense and administer.

In general, one of the major disadvantages of formulations based on emulsions system is that in contrast to single phase systems, emulsion systems may be more complex and difficult to manufacture, especially in sterile form. Frequently, they are not readily sterilisable by thermal treatment without negative impact on their physical properties. Emulsions are also inherently unstable, and could phase separate with time or fluctuations in storage conditions. They, as with all aqueous based systems, are more prone to microbial contamination during use as well. The aseptic processing of emulsions is complex, costly, and is associated with higher risks of failure, i.e. microbial contamination.

Retinoid (Vitamin A) derivatives are another class of hydrocarbon compounds comprising high levels of polyunsaturation, and which are also prone to degradation via oxidation pathways. Retinoid derivatives include retinol, retinal, retinoic acid, tretinoin, isotretinoin, alitretinoin, and related derivatives. Vitamin A derivatives have been used for the treatment of inflammation in relation to the cornea, conjunctiva and other mucosal and epithelial tissues, including conditions such as dry eye disease.

US2012/0095097 for example discloses aqueous ophthalmic compositions comprising Vitamin A, at least 0.4 w/v % of polyoxyethylene polypropylene glycol and trometamol. Antioxidants such as dibutylhydroxytoluene and α-tocopherol acetate, may also be present in these compositions. These compositions are based on micelles of Vitamin A, which is presumably shielded and stabilized by non-ionic surfactant polyoxyethylene polypropylene glycol. These compositions are not preserved as such.

In principle, these preparations would require, if they were to be presented in multi-dose containers which are in principle more cost-efficient and convenient for patients than single-use vials, preservation in order to ensure their microbiological quality. The same would be applicable to all aqueous-based preparations. At the same time however, preservatives which can be used in ophthalmic formulations are potentially damaging to the eye, in particular to the ocular surface, and should be avoided especially in the context of dry eye disease. At least in earlier years, multi-dose formulations for ophthalmic administration had to be preserved using a physiologically acceptable preservative in order to reduce the risk of microbial contamination and infection.

Most preservatives are however problematic for DED patients in that they have a potential to negatively affect the ocular surface, thus counteracting the therapeutic intent. This is particularly relevant for patients with moderate to severe dry eye disease symptoms who may require frequent use for symptom relief, as well as patients who require multiple preserved topical medicaments.

As an alternative, single-dose containers are the main option for the administration of non-preserved formulations such as those used for the Remogen® Omega product. These are however less cost-efficient and convenient to handle for the patient than the conventional multi-dose bottle. Whilst ophthalmic formulations utilizing 'vanishing' preservatives such as sodium chlorite or sodium perborate, which can convert to non-toxic ions and water after instillation and contact with the tear film may also be an option, these may still be irritating to patients especially those with severe disease who may not have sufficient tear volume to effectively degrade the preservatives.

WO 2011/073134 discloses ophthalmic topical pharmaceutical compositions comprising immunosuppressant macrolides such as ciclosporin A and semifluorinated alkanes, for treatment of keratoconjunctivitis sicca. The semifluorinated alkanes in the disclosed compositions serve as suitable liquid vehicles for delivering the therapeutic pharmaceutical agent to the eye, and in particular have a high capacity for dissolving extremely challenging poorly soluble compounds such as ciclosporin. However, there is no mention of the ability of semifluorinated alkanes to stabilize oxidation-sensitive compounds over an extended period of time.

It is therefore an object of the present invention to provide a novel composition which comprising one or more active compounds comprising more than one aliphatic double prone to oxidation, and which at the same time addresses and overcomes the various issues and at least one of the limitations or disadvantages associated with prior art formulations. In a specific aspect, it is an object of the invention to provide an ophthalmic composition for the treatment or prevention of a condition or disease such as dry eye or conditions relating to the inflammation of the ocular tissue. In a further aspect, it is an object of the invention to provide a method of stabilizing an active compound with more than one aliphatic double bond prone to oxidation which does not exhibit one or more of the disadvantages of prior art. Further objects of the invention will become clear on the basis of the following description, examples, and patent claims.

SUMMARY OF THE INVENTION

In a first aspect, the present invention provides a stable liquid composition comprising an active compound with more than one aliphatic double bond prone to oxidation, wherein the active compound is dissolved, dispersed or suspended in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20. The liquid vehicle is substantially free of water.

In one of the embodiments, the composition of the invention comprises a polyunsaturated fatty acid or derivative thereof, in particular an ester derivative. It is further preferred that the polyunsaturated fatty acid or derivative is selected from an omega-3 or omega-6 fatty acid or derivative, such as an omega-3 or omega-6 fatty acid ester, or a mixture thereof. In a further preferred embodiment, said omega-3 or omega-6 fatty acids are selected from docosahexaenoic acid or eicosapentaenoic acid and ester derivatives thereof.

In a further aspect, the invention provides the use of such compositions as a medicament, wherein the medicament may be topically administered to the eye or ophthalmic tissue, and/or wherein the medicament may be used for the treatment of a condition or disease of an eye or ophthalmic tissue such as inflammatory conditions of the ophthalmic tissue or keratoconjunctivitis sicca (dry eye).

In yet a further aspect, the invention provides a method of stabilizing an active compound with more than one aliphatic double bond prone to oxidation comprising the step of dissolving, dispersing, suspending the active compound in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20, and wherein the liquid vehicle is substantially free of water. In one of the preferred embodiments, the active compound is an omega-3 or an omega-6 fatty acid or an ester derivative thereof.

DETAILED DESCRIPTION OF THE INVENTION

In a first aspect, the invention provides a stable liquid composition comprising an active compound with more than one aliphatic double bond prone to oxidation. The composition is further characterized in that the active compound is dissolved, dispersed or suspended in a liquid vehicle comprising a semifluorinated alkane as defined in claim 1 and further explained below As used herein, an active compound refers to any type of pharmaceutically, nutraceutically or otherwise health-promoting active compound or derivative that is useful in the prevention, diagnosis, stabilization, treatment, or -generally speaking-management of a condition or disease. A therapeutically effective amount refers to a dose, concentration or strength which is useful for producing a desired pharmacological, nutraceutical or otherwise health-promoting or -supporting effect.

Active compounds with more than one aliphatic double bond prone to oxidation are usually susceptible to degradation and deterioration over time and storage. The aliphatic double bonds of these compounds are featured in configurations that are particularly prone to undergo oxidation reactions, leading to the formation of side products and quantitative loss of active compound over time. The present invention provides methods of stabilizing such active compounds against oxidation, in particular oxidation which may occur and/or be promoted by thermal, photolytic or chemical means, and in the presence of oxygen as may be present in the atmosphere or as introduced to an initially inert environment over time.

As used herein, an aliphatic double bond refers to a carbon-carbon double bond ($C=C$). An active compound with more than one such double bond may have at least two aliphatic double bonds, in particular in a configuration wherein the double bonds are separated by a methylene group ($—CH_2—$). The one or more aliphatic double bonds of the active compounds of the invention may be in the cis (Z) or trans (E) configuration, or combinations thereof. In one embodiment, the active compound of the invention comprises a structural component of the formula $—(HC=CH—CH_2—HC=CH)_x—$, wherein x is an integer ranging from 2 to 10, in particular from 2 to 5.

Active compounds with more than one aliphatic double bond in which the double bonds are separated by a bridging methylene group (also commonly referred to as compounds possessing methylene-interrupted polyenes) include polyunsaturated fatty acids. Polyunsaturated fatty acids are linear carboxylic acids possessing carbon chains with more than one carbon-carbon double bond. These lipophilic lipids are prone to oxidation, especially in the presence of atmospheric oxygen via radical initiated auto-oxidation processes. In an embodiment, the compositions of the invention comprise a polyunsaturated fatty acid with number of carbon atoms ranging from C16 to C24. Derivatives of polyunsaturated fatty acids, such as esters and in particular alkyl esters are within the scope of the invention. It should be understood within the context of the present invention that a reference to any polyunsaturated fatty acid, or group or species thereof, also covers the respective derivatives, in particular the esters, even if not specifically mentioned.

Polyunsaturated fatty acids (often abbreviated as PUFA) include omega fatty acids such as omega-3 fatty acids (also known as ω-3 fatty acids or n-3 fatty acids) and omega-6 fatty acids (also known as ω-6 fatty acids or n-6 fatty acids). Examples of omega-3 fatty acids (also known as ω-3 fatty acids or n-3 fatty acids) include eicosapentaenoic acid (EPA), docosahexaenoic acid (DHA), α-linolenic acid (ALA). Examples of omega-6 fatty acids (also known as ω-6 fatty acids or n-6 fatty acids) include gamma-linolenic acid, linoleic acid, dihomo-gamma-linolenic acid. Derivatives of omega-3 fatty acids or omega-6 fatty acids, such as ester or alkyl ester derivatives are also within the scope of the invention. Particularly preferred alkyl ester derivatives are eicosapentaenoic acid ethyl ester or docasahexaenoic acid ethyl ester. Derivatives of eicosapentaenoic acid or docosahexaenoic acid such as resolvins and neuroprotectins are also suitable as active compounds within the scope of the invention.

In a further embodiment, the active compounds with more than one aliphatic double bond prone to oxidation are compounds comprising a structural component with more than one aliphatic double bond in linear conjugation with one another. Active compounds comprising more than one aliphatic double bond in linear conjugation are also commonly referred to as polyenes. Preferably, the active compound comprises at least three, or more preferably four or five linearly conjugated double bonds Preferably, the active compounds structurally comprise a conjugated triene, tetraene, pentaene, hexaene or heptaene component. In one embodiment, the active compound comprising a polyene component may be a macrocycle, wherein the polyene or the linearly conjugated double bonds form part of the cyclic structure. The one or more linearly conjugated aliphatic double bonds may be in the cis (Z) or trans (E) configuration, or combinations thereof.

Examples of active compounds comprising more than one linearly conjugated double bond include, but are not limited to, lipophilic vitamin derivatives such as retinoids and derivatives thereof. This class of compounds are also unstable towards prolonged storage and prone to degradation through oxidative pathways such as auto-oxidation. Retinoids and retinoid derivatives (also often referred to as Vitamin A derivatives) include retinol, retinoic acid and its esters (e.g. retinol palmitate or retinol acetate), retinal, tretinoin, isotretinoin, and alitretinoin.

Further examples of active compounds also comprising linearly conjugated double bond systems sensitive and or prone to radical-mediated oxidative degradation with oxygen include sirolimus (rapamycin), a macrolide immunosuppressant drug compound whose structure contains three contiguous double bonds.

Moreover, polyene compounds are contemplated as oxidation-sensitive active ingredients according to the invention, in particular polyene antifungals. In one embodiment, the composition comprises a polyene antifungal such as nystatin, natamycin or amphotericin dissolved in a liquid carrier substantially consisting of one or more semifluorinated alkanes as described herein.

The compositions of the invention may optionally further comprise a carotenoid or carotenoid derivative, in particular a xanthophyll. These compounds also possess poly-conjugated double bond systems. Particularly preferred are lutein and zeaxanthin. Derivatives of lutein or zeaxanthin, such as lutein or zeaxanthin esters are also considered. In a particular embodiment, liquid compositions comprising at least two or more semifluorinated alkanes further comprise lutein or a derivative thereof.

In a further embodiment, the composition comprises ciclopirox olamine as active ingredient. Preferably, ciclopirox olamine is incorporated in the dissolved state. As will be discussed in more detail below, some of the key advantages of the present invention are brought about by the presence of a semifluorinated alkane in the composition as liquid vehicle, or part of the liquid vehicle, for active compounds such as polyunsaturated fatty acids, retinoids, or other active compounds with more than one aliphatic double bond prone to oxidation.

Semifluorinated alkanes are linear or branched alkanes some of whose hydrogen atoms have been replaced by fluorine. In a preferred embodiment, the semifluorinated alkanes (SFAs) used in the present invention are composed of at least one non-fluorinated hydrocarbon segment and at least one perfluorinated hydrocarbon segment. Particularly useful are SFAs which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFAs having two or three segments as RFRH and RFRHRF, respectively, wherein $R_F$ designates a perfluorinated hydrocarbon segment, $R_H$ designates a non-fluorinated segment. Alternatively, the compounds may be referred to as FnHm and FnHmFo, respectively, wherein F means a perfluorinated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are integers independently selected from the range of 3 to 20. SFAs which are useful in the context of the present invention are also described in EP-A 965 334, EP-A 965329 and EP-A 2110126, the disclosure of which documents is incorporated herein.

In a further embodiment, the compositions of the invention comprise a semifluorinated alkane according to the formula $F(CF_2)_n(CH_2)_mH$, wherein n and m are integers independently selected from the range of 3 to 20. In another particular embodiment, n is an integer from the range of 3 to 8 and m is an integer from the range of 3 to 10. In yet another particular embodiment, the semifluorinated alkane is a compound according to the formula $F(CF_2)_n(CH_2)_mH$ wherein n is an integer from the range of 6 to 20 and m is an integer from the range of 10 to 20. Most preferably, the semifluorinated alkane is a liquid. Preferred SFAs include, in particular, the compounds $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$. Further preferred SFAs include, in particular, $F(CF_2)_8(CH_2)_{10}H$ and $F(CF_2)_{10}(CH_2)_{12}H$.

In a further embodiment, the composition may comprise more than one SFA. Preferably, compositions comprising more than one SFA comprise at least one of SFAs selected from $F(CF_2)_4(CH_2)_5H$, $F(CF_2)_4(CH_2)_6H$, $F(CF_2)_4(CH_2)_3H$, $F(CF_2)_6(CH_2)_4H$, $F(CF_2)_6(CH_2)_6H$, $F(CF_2)_6(CH_2)_8H$, and $F(CF_2)_6(CH_2)_{10}H$. In another embodiment, the composition comprises at least two SFAs selected compounds $F(CF_2)_4(CH_2)_5H$, $F(CF_2)_4(CH_2)_6H$, $F(CF_2)_4(CH_2)_3H$, $F(CF_2)_6(CH_2)_4H$, $F(CF_2)_6(CH_2)_6H$, $F(CF_2)_6(CH_2)_8H$, and $F(CF_2)_6(CH_2)_{10}H$, and at least one of $F(CF_2)_3(CH_2)_{10}H$ and $F(CF_2)_{10}(CH_2)_{12}H$. In one of the preferred embodiments, the composition comprises a first semifluorinated alkane of formula $F(CF_2)_n(CH_2)_mH$, wherein n is an integer from the range of 3 to 8 and m is an integer from the range of 3 to 10 and a second semifluorinated alkane of the formula $F(CF_2)_n(CH_2)_mH$ wherein n is an integer from the range of 6 to 20 and m is an integer from the range of 10 to 20.

As mentioned, the compositions comprise an active compound with more than one aliphatic double prone to oxidation, wherein the active compound is dissolved, dispersed or suspended in a liquid vehicle comprising a SFA that is substantially free of water. In some embodiments, the liquid vehicle comprising a SFA may further comprise other organic liquids or other excipients, but is effectively free of water.

According to a particular embodiment, the active compounds of the invention may be dissolved, that is, in complete solvation or solution in a liquid vehicle comprising a semifluorinated alkane. Alternatively, the active compounds may be dispersed or suspended in a liquid vehicle comprising a semifluorinated alkane. As used herein, dispersing means the formation of a system having at least one continuous (or coherent) phase and at least one discontinuous (or inner) phase which is dispersed in the continuous phase. The term dispersion is understood to include colloidal systems in which the active compound is finely dispersed in the liquid phase. It is also understood that a suspension is a type of dispersion, in which the dispersed phase is in the solid state. The suspensions useful for practicing the invention are liquids, at least at physiological temperature, which means that the continuous phase is liquid. Typically, suspensions are liquid at room temperature.

Liquid SFAs are chemically and physiologically inert, colourless and stable. Their typical densities range from 1.1 to 1.7 g/cm³, and their surface tension may be as low as 19 mN/m. SFAs of the $F(CF_2)_n(CH_2)_mH$ type are insoluble in water but also somewhat amphiphilic, with increasing lipophilicity correlating with an increasing size of the non-fluorinated segment. Liquid SFAs of this type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. This and other applications have established SFAs as physiologically well tolerated compounds.

It has also been proposed that SFAs have high solubility for gases such as oxygen, and may act as oxygen carriers (U.S. Pat. No. 6,262,126). Experimentally, they have been used as blood substitutes, as oxygen-carriers (H. Meinert et al., Biomaterials, Artificial Cells, and Immobilization Biotechnology, Vol. 21(5), pp. 583-95, 1993).

In contradiction to such facts and teachings, the inventors have found that liquid compositions comprising SFAs and the oxidation-sensitive active compounds, such as those described above, are surprisingly stable under ambient as well as non-ideal conditions (as illustrated by the examples further below).

The inventors have found that a method of stabilising a compound of the invention can simply comprise the step of dissolving, dispersing, or suspending an active compound of the invention in a liquid vehicle comprising a semifluorinated alkane, as no additional antioxidants or other active compound stabilizers, as are typically used for the formulation of such compounds are required. This simplification can be advantageous for various medical uses of the composition involving especially, frequent administration to tissues such as ocular or mucosal tissues. These generally have poor tolerability to a wide variety of antioxidants and stabilizers and generally do not benefit from frequent exposure to such excipients.

In one embodiment, a method of stabilising a polyunsaturated fatty acid or an ester derivative thereof comprises the step of dissolving, dispersing or suspending the polyunsaturated fatty acid or an ester derivative thereof in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. In yet a further embodiment, said method of stabilisation comprises the step of dissolving, dispersing, or suspending a polyunsaturated fatty acid selected from an omega-3 or an omega-6 fatty acid or ester derivatives, or mixtures thereof in a liquid vehicle comprising a semifluorinated alkane selected from $F(CF_2)_4(CH_2)_5H$, $F(CF_2)_4(CH_2)_6H$, $F(CF_2)_4(CH_2)_3H$, $F(CF_2)_6(CH_2)_4H$, $F(CF_2)_6(CH_2)_6H$, $F(CF_2)_6(CH_2)_3H$, and $F(CF_2)_6(CH_2)_{10}H$.

Further embodiments within the scope of the invention are stable liquid compositions consisting of essentially one or more omega-3 fatty acids or derivatives thereof dissolved or dispersed in a liquid semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. Compositions comprising no further active compounds other than omega-3 fatty acid or derivatives thereof are also within the scope of the invention. Preferred are stable liquid compositions consisting of one or more omega-3 fatty acid selected from α-linolenic acid, docosahexaenoic acid, or eicosapentaenoic acid and ester derivatives thereof, wherein the omega-3 fatty acid or ester derivative thereof is dissolved or dispersed in a semifluorinated alkane of the invention, for instance, $F(CF_2)_6(CH_2)_8H$. In a further preferred embodiment, the liquid composition consists essentially of docosahexaenoic acid and/or eicosahexaenoic acid or ester derivatives thereof dissolved in or dispersed in $F(CF_2)_6(CH_2)_8H$.

In a particular embodiment, liquid compositions comprising at least two or more semifluorinated alkanes further comprise one or more omega-3-fatty acid or omega-3-fatty acid derivative, and/or omega-6 fatty acid or omega-6 fatty acid derivative.

Also contemplated are methods of stabilizing a retinoid selected from retinol, retinoic acid, retinal, tretinoin, isotretinoin, and alitretinoin or derivatives thereof, or sirolimus, or a polyene compound, or ciclopirox olamine, comprising the step of dissolving, dispersing or suspending said compounds in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. In another embodiment, method of stabilising a retinoid selected from retinol, retinoic acid, retinal, tretinoin, isotretinoin, and alitretinoin or derivatives thereof, or sirolimus, comprises the step of dissolving, dispersing or suspending said compounds in a liquid vehicle comprising a semifluorinated alkane selected from $F(CF_2)_4(CH_2)_5H$, $F(CF_2)_4(CH_2)_6H$, $F(CF_2)_4(CH_2)_3H$, $F(CF_2)_6(CH_2)_4H$, $F(CF_2)_6(CH_2)_6H$, $F(CF_2)_6(CH_2)_8H$, and $F(CF_2)_6(CH_2)_{10}H$.

In a further embodiment of the invention, liquid compositions comprising at least two or more semifluorinated alkanes further comprise at least one solubilized lipophilic vitamin or vitamin derivative.

The liquid compositions comprising an active compound with more than one aliphatic double bond prone to oxidation dissolved, dispersed or suspended in a liquid vehicle comprising a semifluorinated alkane as described previously, wherein the liquid vehicle is substantially free of water may comprise at least about 0.01-10 wt. % of active compound. Preferably, the compositions comprise at least about 1 wt. % of active compound relative to the weight of the composition, such as about 2 wt % or more, or at least 5 wt %.

The compositions of the present invention are useful as medicaments, in particular as medicaments topically administered to an eye or ophthalmic tissue, to the skin, or to the buccal, anal, vaginal, or nasal mucosa.

The SFA component of the liquid vehicle of these compositions exhibit properties rendering them particularly amenable for ophthalmic applications. Many of the SFAs as defined herein have refractive indices close to water. In one of the specific embodiments, the invention is therefore practised with an SFA whose refractive index is from 1.29 to 1.35, and in particular from about 1.30 to about 1.35 at 20° C.

Moreover, SFAs according to the invention exhibit a remarkable wetting and spreading behaviour by which they can rapidly and effectively spread over the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

SFAs according to the invention exhibit excellent wetting of various surfaces. For example, the contact angle of both F4H5 and F6H8 on tablets compressed from either trospium chloride or fenofibrate (150 mg of drug substance compressed at 15-20 kN to tablets of 13 mm in diameter) is not measurable, i.e. there is perfect wetting. It is noted that fenofibrate is an example of a hydrophobic, poorly water-soluble compound, whereas trospium chloride is hydrophilic and water-soluble. For comparison, the contact angle of purified water on the fenofibrate tablet was determined as 92.5°, i.e. the tablet was poorly wetted by water.

In addition, SFAs according to the invention are also capable of forming very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct.

The invention also provides a means of formulating non-aqueous ophthalmic compositions which are microbiologically stable. Aqueous ophthalmic compositions are prone to bacterial contamination. In comparison, SFAs according to the invention have bacteriostatic properties and do not support microbial growth. Hence, it is possible to formulate preservative-free ophthalmic compositions which are better tolerable for many patients suffering from eye conditions that are readily exacerbated by preservatives or other excipients that may irritated through repeated exposure.

The compositions of the invention are thus very well suited for the topical administration to an eye or ophthalmic tissue. Ophthalmic tissue includes any surface of the eye anatomy that is, or can be (i.e. by non-surgical means) topically exposed. Preferably, the compositions are administered to the cornea or conjunctiva. The compositions are also preferably administered to the upper or lower eye lid margins, meibomian gland ducts, eyelashes or any area of the eye or eye lid anatomy.

In particular, it is contemplated that these compositions can be used for the treatment of a condition or disease of an eye or ophthalmic tissue, such as inflammatory conditions of the ophthalmic tissue or keratoconjunctivitis sicca (dry eye) or symptoms or conditions associated therewith. According to an embodiment of the invention, a composition consisting of a semifluorinated alkane of the formula $F(CF_2)_n(CH_2)_mH$, wherein n is an integer from the range of 3 to 8 and m is an integer from the range of 3 to 10, and optionally one or more further excipients may be used as a medicine in the treatment of keratoconjunctivitis sicca (dry eye) or a symptom or condition associated therewith Keratoconjunctivitis sicca is a complex, multifaceted disease or condition as described above. Aqueous-deficient DED, evaporative DED are within the scope of keratoconjunctivitis sicca and form specific subtypes thereof. Sjogren syndrome, lacrimal gland insufficiency, meibomian gland disease and meibomian gland dysfunction, and other conditions are also associated with keratoconjunctivitis sicca, being direct or indirect causes thereof, and may be treated with the composition of the invention.

Meibomian gland diseases cover a broad range of meibomian gland disorders including neoplasia and congenital disorders. Meibomian gland dysfunction, on the other hand is understood to be abnormalities of the meibomian glands which are often characterized by gland duct obstructions and/or changes (qualitative and/or quantitative) to the secretions of the glands. In general, conditions or disease states causing or leading to an abnormal, reduced or increased delivery of lipids to the tear film can give rise to keratoconjunctivitis sicca and the symptoms associated therewith.

Symptoms of keratoconjunctivitis sicca include a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing. In addition to the symptoms of keratoconjunctivitis sicca as described, patients with meibomian gland dysfunction may also experience symptoms including itchiness, redness, swelling, pain or soreness, discharge accumulation or crusting specifically at the lid margins. It is understood that not all patients suffering from keratoconjunctivitis sicca exhibit all symptoms simultaneously. Hence, there is currently no uniform set of criteria for diagnosing the disease. It is also understood that patients may suffer from one or more subtypes of keratoconjunctivitis sicca, or one or more conditions or disease pathways causing keratoconjunctivitis sicca. It is however important to note that, within the scope of the present invention, any of the aspects, symptoms or pathophysiological consequences of dry eye disease may be addressed.

The compositions of the invention may also comprise one or more active compounds and/or further excipients as are required or useful. In an embodiment, the compositions of the invention may further comprise an anti-inflammatory compound selected from the group of NSAIDs, corticosteroids, and immunomodulators. In particular, such compositions may be useful as a medicament for topical administration to an eye or ophthalmic tissue, especially as medicaments for treatment of inflammatory conditions of ophthalmic tissue or keratoconjunctivitis sicca (dry eye), or a symptom or condition associated therewith. Preferred immunomodulators are calcineurin inhibitors (e.g. cyclosporin or tacrolimus) or mTOR inhibitors (e.g. sirolimus). Preferred NSAIDS include flurbiprofen, diclofenac, indometacin, bromfenac, nepafenac, ketoprofen, and ketorolac and salts and derivatives thereof. Preferred corticosteroids include prednisolone, loteprednol, dexamethasone, hydrocortison, rimexolone, fluorometholone and salts and derivatives thereof. These further active compounds are preferably also dissolved or dispersed in a liquid semifluorinated alkane of the invention.

In another embodiment, the compositions of the invention may also further comprise one or more flavan-3-ols such as catechins. Catechin or catechin isomers (e.g. epicatechin) and derivatives (for example, ester derivatives of catechin) are particularly preferred.

In terms of further excipients, if any, especially preferred are those that are biocompatible and are tolerated by the eye, and which are liquid and/or soluble and miscible in SFAs In particular, excipients are preferably selected from lipids, oils, lubricants, lipophilic vitamins, viscosity agents, antioxidants, surfactants and mixtures of two or more thereof.

Examples of potentially useful lipids and oily excipients and which may be included in the compositions of the invention include triglyceride oils (e.g. soybean oil, olive oil, sesame oil, cotton seed oil, castor oil, sweet almond oil), mineral oil (e.g. petrolatum and liquid paraffin), medium chain triglycerides (MCT), oily fatty acids, isopropyl myristate, oily fatty alcohols, esters of sorbitol and fatty acids, oily sucrose esters, oily cholesterol esters, oily wax esters, glycerophospholipids, sphingolipids, or any oily substance which is physiologically tolerated by the eye. Any synthetic, semi-synthetic or natural oily excipients which mimic or are structurally analogous or related to the components naturally found in the tear film lipid layer are also within the scope of the invention.

Examples of potentially useful lipophilic vitamin excipients include vitamin E (e.g. α-tocopherol) and their derivatives (e.g. tocotrienols) and esters (e.g. tocopherol acetate or tocopherol TPGS). In an embodiment, liquid compositions of the invention may further comprise at least one lipophilic vitamin excipient that is completely solubilized.

Examples of potentially useful lubricants and/or viscosity agents include carboxymethyl cellulose, hydroxymethyl cellulose, hydroxypropyl cellulose, glycerol, polyvinyl alcohol, polyethylene glycol, propylene glycol, hyaluronic acid, hydroxypropyl guar.

In one of the embodiments, the composition of the invention is free of surfactants. In an alternative embodiment, and depending on the specific active ingredient to be formulated, a small amount of a physiologically acceptable surfactant may be incorporated. Potentially useful surfactant excipients include in particular non-ionic surfactants or amphiphilic lipids. Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

The composition may of course comprise further excipients as required or useful such as acids, bases, electrolytes, buffers, solutes, stabilisers, synergists, and—if required in a particular case—a preservative. In one of the embodiments, however, the composition is free of preservatives.

The compositions may be formulated to be administered as a liquid solution, gel, suspension, or spray. They may be prepared by commonly known techniques for the manufacture of said liquid solutions, gels, suspensions, or sprays.

Furthermore, the invention provides a pharmaceutical kit comprising the composition as described above and a container holding the composition. Preferably, the container which contains the composition has a dispensing means such as a dropping device adapted for topically administering the composition to the eye of a patient.

The following examples serve to illustrate the invention; however, these are not to be understood as restricting the scope of the invention.

EXAMPLES

Example 1

Solutions of the omega-3 fatty acid esters, eicosapentaenoic acid ethyl ester (EPA-EE) and docosahexenoic acid ethyl ester (DHA-EE), were prepared in $F(CF_2)_6(CH_2)_8H$ at concentrations of 1.0 wt % and 5.0 wt %.

Solutions containing a mixture of 1 wt % each of DHA-EE and EPA-EE (total 2.0 wt % of active compound) and 5.0 wt % of a combination of the DHA-EE and EPA-EE, at a ratio of approx. 2:3 in $F(CF_2)_6(CH_2)_8H$ were also prepared. The solutions were filled in crimped vials and stored at 2-8° C., at 25° C./60% RH, and at 40° C./75% RH for the purpose of conducting a 6 month stability programme. The results obtained after a 13-week period are reported herein.

Samples were taken from the vials at intervals for GC analysis (See Tables 1-3 for result) of the compositions. The remaining percentages of other components detected by GC (FID) but not shown here in the tables are attributed to impurities already present in the original samples of omega-3 fatty ester or the SFA vehicle before formulation. No rise in the level of impurities was observed over the course of the stability program.

No significant observable changes in the content of the omega-3 fatty acid esters were detected under all temperatures tested. Results were more or less also comparable across different batches at all storage conditions. In the following tables, the content of the active ingredient is presented as percentage relative to the initial content.

TABLE 1

Content of active compound (%) after storage at 2-8° C.

| Compound | After 4 weeks |
|---|---|
| 1.0 wt % EPA-EE | 99.6 |
| 1.0 wt % DHA-EE | 99.5 |
| 5.0 wt % EPA-EE | 99.9 |
| 5.0 wt % DHA-EE | 101.5 |
| 2.0 wt % EPA-EE/DHA-EE | 100.2/99.7 |
| 5.0 wt % EPA-EE/DHA-EE | 100.3/99.5 |

TABLE 2

Content of active compound (%) after storage at: 25° C./60% RH

| Compound | After 4 weeks | After 13 weeks |
|---|---|---|
| 1.0 wt % EPA-EE | 99.6 | 99.0 |
| 1.0 wt % DHA-EE | 99.6 | 99.4 |
| 5.0 wt % EPA-EE | 99.8 | 99.5 |
| 5.0 wt % DHA-EE | 99.8 | 103.2[1] |
| 2.0 wt % EPA-EE/DHA-EE | 100.2/99.6 | 100.5/98.6 |
| 5.0 wt % EPA-EE/DHA-EE | 101.1/98.0 | 103.5/92.6 |

[1]Slight increase probably due to impurities with elution times similar to DHA-EE

TABLE 3

Content of active compound (%) after storage at 40° C./75% RH

| Compound | 1 week | 2 weeks | 4 weeks | 8 weeks | 13 weeks |
|---|---|---|---|---|---|
| 1.0 wt % EPA-EE | 99.6 | 99.6 | 99.6 | 99.4 | 97.3 |
| 1.0 wt % DHA-EE | 99.9 | 99.8 | 99.8 | 99.6 | 99.1 |

TABLE 3-continued

Content of active compound (%) after storage at 40° C./75% RH

| Compound | 1 week | 2 weeks | 4 weeks | 8 weeks | 13 weeks |
|---|---|---|---|---|---|
| 5.0 wt % EPA-EE | 99.9 | 99.9 | 99.8 | 99.4 | 98.7 |
| 5.0 wt % DHA-EE | 99.9 | 100.0 | 100.0 | 99.9 | 100.0 |
| 2.0 wt % EPA-EE/DHA-EE | 101.8/98.2 | 100.3/99.6 | 100.5/99.0 | 100.8/98.3 | 100.8/98.2 |
| 5.0 wt % EPA-EE/DHA-EE | 100.9/98.3 | 101.0/98.0 | 101.6/96.6 | 103.1/93.1 | 105.4/88.4 |

The invention claimed is:

1. A stable liquid composition comprising an active compound with more than one aliphatic double bond prone to oxidation, wherein the active compound is dissolved in a liquid vehicle comprising a semifluorinated alkane of formula $$F(CF_2)_n(CH_2)_mH$$

wherein n and m are integers independently selected from the range of 3 to 20, and wherein the liquid vehicle is substantially free of water; and
wherein the active compound is an omega-3 or omega-6 fatty acid or derivative thereof, or a mixture of omega-3 or omega-6 fatty acids or derivatives thereof;
and wherein the composition comprises about 0.01-10 wt. % of the active compound.

2. The composition of claim 1, wherein the active compound is a polyunsaturated fatty acid derivative which is an ester.

3. The composition of claim 1, wherein the active compound is an omega-3 fatty acid selected from α-linolenic acid, docosahexaenoic acid, eicosapentaenoic acid, and ester derivatives thereof.

4. The composition of claim 3, wherein the composition consists essentially of the one or more omega-3 fatty acids or ester derivatives thereof dissolved in the liquid semifluorinated alkane.

5. The composition of claim 4, wherein the composition consists essentially of docosahexaenoic acid and/or eicosapentaenoic acid or alkyl ester derivatives thereof dissolved in a semifluorinated alkane of the formula $F(CF_2)_6(CH_2)_8H$.

6. The composition of claim 3, wherein the semifluorinated alkane is selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, $F(CF_2)_6(CH_2)_{10}H$, $F(CF_2)_8(CH_2)_{1014}$ and $F(CF_2)_{10}(CH_2)_{12}H$.

7. The composition of claim 6, wherein the active compound is an omega-3 fatty acid or derivative thereof.

8. The composition of claim 7, wherein the omega-3 fatty acid or derivative thereof is selected from one or more of docosahexaenoic acid, eicosapentaenoic acid, and alkyl ester derivatives thereof.

9. The composition of claim 8, wherein the omega-3 fatty acid or derivative thereof is selected from docosahexaenoic acid ethyl ester or eicosapentaenoic acid ethyl ester.

10. The composition of claim 1, wherein the semifluorinated alkane is selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, $F(CF_2)_6(CH_2)_{10}H$, $F(CF_2)_8(CH_2)_{10}H$ and $F(CF_2)_{10}(CH_2)_{12}H$.

11. The composition of claim 1, further comprising a lipid or oily excipient selected from triglyceride oils, mineral oil, medium chain triglycerides, oily fatty acids, isopropyl myristate, oily fatty alcohols, esters of sorbitol and fatty acids, oily sucrose esters, oily cholesterol esters, oily wax esters, glycerophospholipids, and sphingolipids.

12. The composition of claim 1, further comprising an anti-inflammatory compound selected from the group of NSAIDs, corticosteroids and immunomodulators.

13. The composition of claim 1, wherein the composition comprises an omega-3 fatty acid or derivative thereof, and wherein the omega-3 fatty acid or derivative thereof is the only active ingredient in the composition.

14. The composition of claim 1, wherein the composition comprises an omega-3 fatty acid derivative selected from a derivative of eicosapentaenoic acid, a derivative of docosahexaenoic acid, a resolvin, and a neuroprotectin.

15. The composition of claim 1, wherein the composition is microbiologically stable and does not comprise a preservative.

16. A method of treating a disease or condition of a patient in need of such treatment, comprising administering an effective amount of the composition of claim 1 to the patient, wherein the composition is topically administered to an eye or ophthalmic tissue, to the skin, or to the buccal, anal, vaginal, or nasal mucosa.

17. The method of claim 16, wherein the disease or condition is a condition or disease of an eye or ophthalmic tissue.

18. The method of claim 17, wherein the disease or condition is an inflammatory condition of the ophthalmic tissue or keratoconjunctivitis sicca (dry eye).

19. A method of stabilising an active compound with more than one aliphatic double bond prone to oxidation comprising the step of dissolving the active compound in a liquid vehicle comprising a semifluorinated alkane of formula $$F(CF_2)_n(CH_2)_mH$$

wherein n and m are integers independently selected from the range of 3 to 20 and wherein the liquid vehicle is substantially free of water;
wherein the active compound is an omega-3 or omega-6 fatty acid or derivative thereof, or a mixture of omega-3 or omega-6 fatty acids or derivatives thereof;
and wherein the composition comprises about 0.01-10 wt. % of the active compound.

20. The method of claim 19, wherein the semifluorinated alkane is selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, $F(CF_2)_6(CH_2)_{10}H$, $F(CF_2)_8(CH_2)_{1014}$ and $F(CF_2)_{10}(CH_2)_{12}H$.

* * * * *

UNITED STATES PATENT AND TRADEMARK OFFICE
CERTIFICATE OF CORRECTION

PATENT NO. : 9,770,508 B2
APPLICATION NO. : 14/427969
DATED : September 26, 2017
INVENTOR(S) : Bernhard Günther, Dieter Scherer and Anthony Pettigrew Page 1 of 1

It is certified that error appears in the above-identified patent and that said Letters Patent is hereby corrected as shown below:

In the Claims

At Column 15, Line 46: In Claim 6, please replace "$F(CF_2)_8(CH_2)_{1014}$" with "$F(CF_2)_8(CH_2)_{10}H$".

At Column 16, Line 60: In Claim 20, please replace "$F(CF_2)_8(CH_2)_{1014}$" with "$F(CF_2)_8(CH_2)_{10}H$".

Signed and Sealed this
Twenty-second Day of May, 2018

Andrei Iancu
*Director of the United States Patent and Trademark Office*